United States Patent [19]

Mathisen

[11] 4,101,222

[45] Jul. 18, 1978

[54] SPECTROPHOTOMETER SAMPLE HOLDER WITH IMPROVED SAMPLE VIEWING APPARATUS

[75] Inventor: Einar Skau Mathisen, Poughkeepsie, N.Y.

[73] Assignee: International Business Machines Corporation, Armonk, N.Y.

[21] Appl. No.: 753,769

[22] Filed: Dec. 23, 1976

[51] Int. Cl.² .......................... G01N 21/16; G01J 3/42
[52] U.S. Cl. ................................. 356/244; 350/287; 356/96; 356/173; 356/210
[58] Field of Search ................. 356/244, 96, 173, 176, 356/177, 209, 210; 350/286, 287

[56] References Cited

U.S. PATENT DOCUMENTS

| 3,887,791 | 6/1975 | Kitchens | 350/112 |
| 3,986,778 | 10/1976 | Mathisen et al. | 356/244 |

Primary Examiner—Vincent P. McGraw
Attorney, Agent, or Firm—William S. Robertson

[57] ABSTRACT

An improved sample holder for a spectrophotometer includes a stationary base that forms a cylindrical cavity and supports a fiber optic head assembly over the cavity for analyzing the color of a sample that is positioned adjacent the base and under the cavity. The fiber optic head assembly covers the top of the cavity and the area of the sample that is to be color analyzed is not visible to an operator of the spectrophotometer. A shutter mechanism is arranged to be moved in an opening in the base between a closed position in which the shutter forms part of the cylindrical wall of the aperture and an open position in which the opening in the base permits an operator to view the sample. A prism is provided to raise the viewing position of the operator to the normal position of the operator.

7 Claims, 3 Drawing Figures

SPECTROPHOTOMETER SAMPLE HOLDER WITH IMPROVED SAMPLE VIEWING APPARATUS

RELATED APPLICATIONS

Application Ser. No. 619,105 of E. N. Giancarlo et al., filed Oct. 2, 1975, for an ornamental design for an "Analytical Instrument System" discloses a textile color analyzer that the apparatus of this invention may be used with. This color analyzer is described in more detail in a publication, *Textile Color Analyzer, Theory-Maintenance,* SY22-6992-1, available from the assignee of this invention.

U.S. Pat. No. 3,986,778 of E. S. Mathisen et al., issued Oct. 19, 1976, for a "Spectrophotometer Sample Holder" discloses a sample holder and has useful background informaton and is incorporated herein by reference.

FIELD OF THE INVENTION

The related patent of Mathisen et al. discloses a spectrophotometer sample holder for analyzing the color of textiles. This apparatus includes a probe head that is a generally disk shaped support for a central fiber optic bundle that transmits light to illuminate the textile sample and peripheral array of fiber optic bundles that transmit reflected light from the textile to a light detector. The probe head is carried on a slider that forms a cavity between the probe head and the textile sample so that the sample and the peripheral fiber bundles are isolated from extraneous sources of light. Thus, the area of the textile that is in a position under the probe head for a color analyzing operation is not viewable by an operator of the color textile analyzer. It is desirable to permit the operator to view the areas to be sampled so that a choice can be made in selecting the area of the textile for the test, as the related patent explains. In the apparatus of the related patent, the slider is mounted on a base and is slideable between an operating position and a preliminary viewing position. The slider has an aperture similar to the cavity that can be located over a selected area of the textile while the operator views the textile. When the slider is moved to the operating position, the probe head moves into the position selected for the test. One object of this invention is to provide a new and improved sample holder in which the probe head is combined with a stationary base which is constructed to permit the operator to view the textile when it is in position for a test.

The related publication shows a stationary probe head and a sample support that can be raised to the probe head assembly for a test and can be lowered to permit the textile to be placed on the support. When the support is in its lower position, the operator can view the subject as it is positioned on the support. In the sample holder that will be described in detail later, additional components of the apparatus would obstruct the view of the sample when the support is lowered. Additionally, it is desirable, as in the related patent of Mathisen et al, to permit the operator to view the subject in a position that is closely similar to the actual test position.

SUMMARY OF THE INVENTION

An object of this invention is to provide a new and improved sample holder for a textile color analyzer that permits an operator to view the test subject in the position in which it will be tested. A more specific object is to provide a new and improved probe head assembly that can be conveniently used by an operator who is seated at the textile color analyzer. The test subject is illuminated by the central illuminating fiber bundle of the probe head or by a supplemental illumination system.

The sample holder of this invention has a stationary base that supports the probe head, and the base has a cavity that establishes the path for illuminating the test sample and for viewing the test sample by means of the fiber optics. The base has an opening that cuts across the cavity, and a shutter mechanism slides in this opening between an open position and a closed position. The shutter has a cylindrical wall that forms a portion of the cavity wall when the shutter is in the closed position. When the shutter is in the open position, the passageway for the shutter is open to the cavity. The base has an opening from its upper surface to the opening for the shutter, and a prism is mounted on the upper surface of the base over the opening. The prism provides a light path between the sample that is held below the cavity and a normal viewing position for an operator. With the improved sample holder, a seated operator of the textile analyzer is provided a convenient and natural appearing image of the area of the portion of the test subject that is within the cavity. The apparatus is easy to operate, and it avoids interference with the normal cavity structure or other components of the probe head assembly.

Other advantages and features of the invention will be apparent from the description of a preferred embodiment of the invention.

THE DRAWING

THE PROBE HEAD ASSEMBLY OF THE DRAWING

Introduction

Figure 1A:
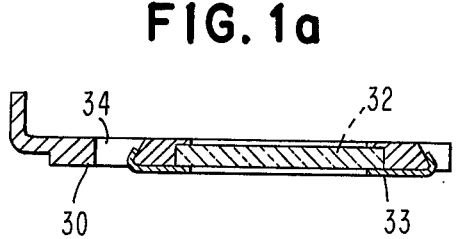
FIG. 1a is a side section of a slide mechanism of the probe head assembly.
Figure 1:
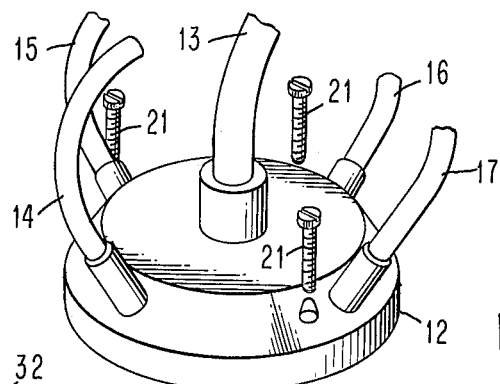
FIG. 1 is a perspective of the probe head assembly of this invention.
Figure 2:
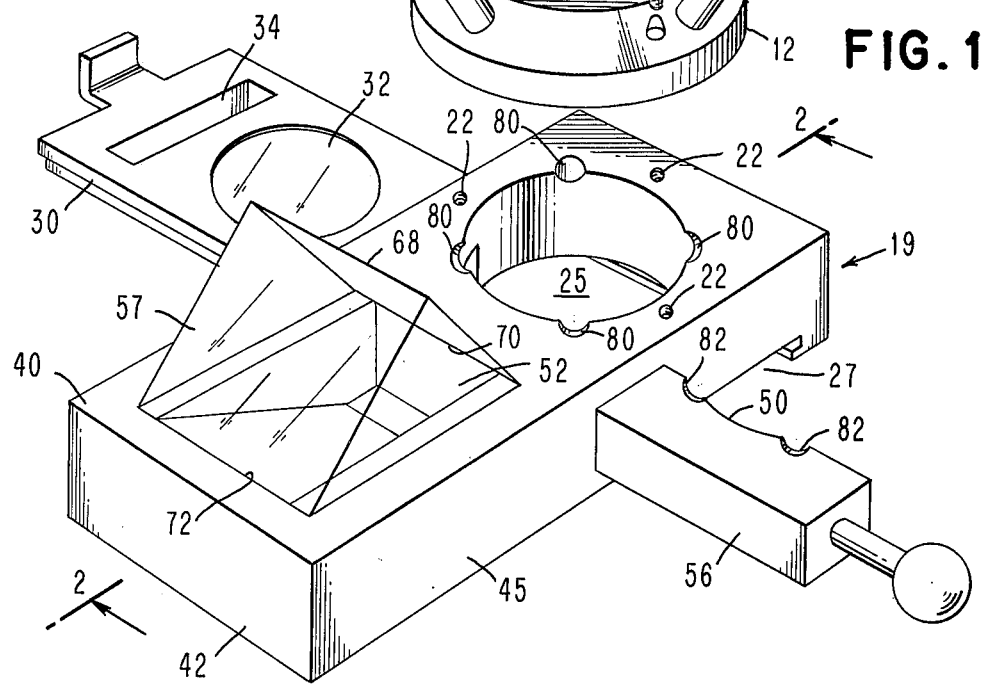
FIG. 2 is a side view of the probe head assembly of FIG. 1 along line 2-2.
Figure 2:
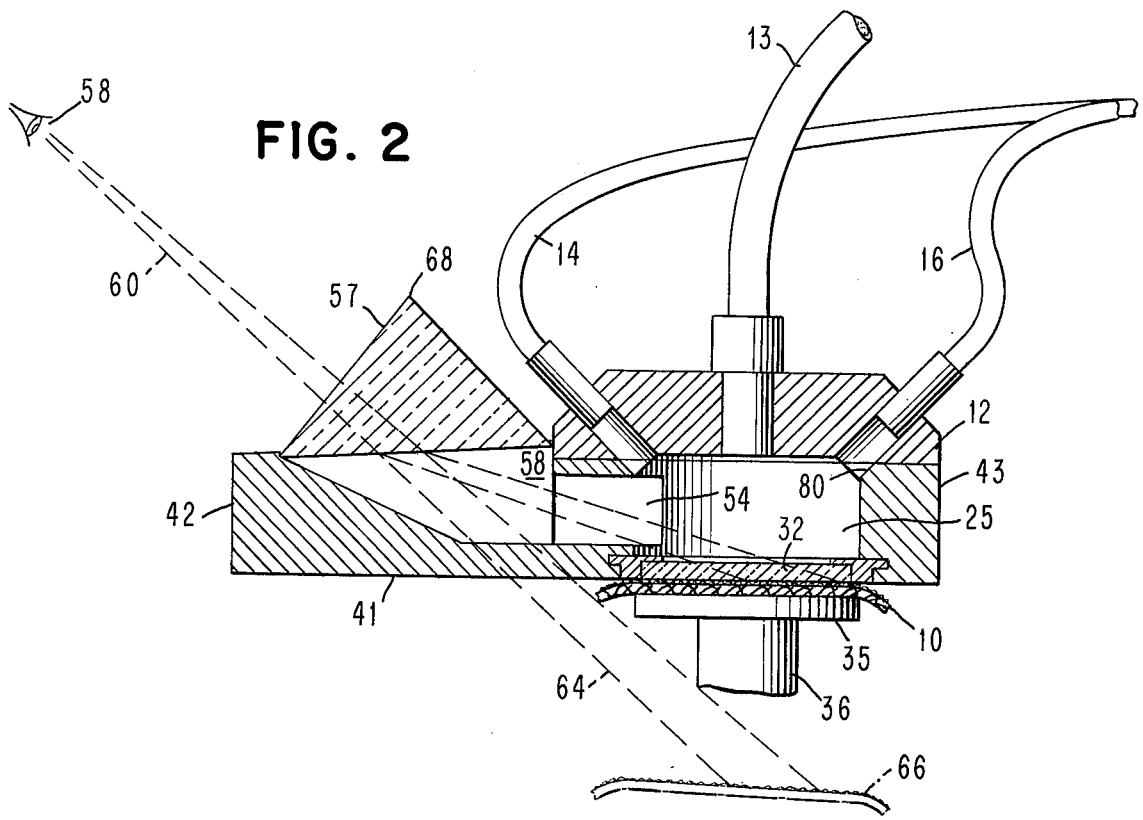

FIG. 2 shows a textile test subject 10 that is to be color analyzed by the apparatus of this invention. Both FIGS. 1 and 2 show the probe head 11 that is described in more detail in the related patent of Mathisen et al. The probe head includes a support 12, a central fiber optic bundle 13 that carries light to illuminate the textile sample and a peripheral array of fiber optic bundles 14 thru 17 that carry light that is reflected from the subject. The probe head is mounted on a base 19 (described later) by means such as screws 21 that are threaded in holes 22 in the base, and it is located over a cavity 25 that is formed in base 19.

Base 19 is also shaped to provide a guideway 27 on its lower surface under the cavity to carry a slide 30 that holds a quartz reference plate 32. The quartz reference plate 32 is supported on a plate 33 that snaps over a sloping end edge of slide 30 and a sloping edge of a rectangular aperture 34 formed in the slide as can be seen in FIG. 1a.

As FIG. 2 shows, the test subject 10 is placed on a disk shaped support 35 that is carried by a rod 36 between the position shown in FIG. 2 and a position in which the rod and support are lowered sufficiently from the lower surfaces of base 19 and side 30 to permit an operator to position the test subject on the support. Suitable means is provided for raising and lowering the support. This means may comprise a handle pivotally mounted at the right of the apparatus of FIG. 2 and a lever connected to the handle to ride against the lower, flat, surface (not shown) of rod 36. Support 35 and the handle (not shown) for raising and lowering the support are both located at a convenient position for an operator who is seated at the color analyzer station. This apparatus is described in the related publication.

The Base Structure

Base 19 is a generally rectangular solid of a suitable material such as steel with upper and lower surfaces 40 and 41, opposite ends 42, 43 and a side 45 and an opposite side that is hidden in the drawing. The base 19 may be supported by suitable means such as screws (not shown) with its end surface 43 against a supporting surface of the color analyzer station.

An optical pathway is formed through base 19 from an opening 52 in upper surface 40 to the cavity 25. This pathway includes a rectangular opening 54 (see FIG. 2) that cuts across a portion of the cavity 25. A shutter 56 slides in rectangular opening 54 between an open position that is shown in FIG. 1 and a closed position. When the shutter 56 is in the open position, the viewing pathway is open between the cavity and the upper surface 40 of base 19. When the shutter 56 is in its closed position, the shutter blocks this pathway.

Shutter 56 includes a generally bar shaped element that has a suitable handle at its outer end. FIG. 1 shows an edge 50 of a cylindrical surface in shutter 56 that forms a portion of the cylindrical wall of cavity 25 when shutter 56 is in the closed position. Shutter 56 may have a small screw at the end that is hidden in FIG. 1 to bear against an inner surface of base 19 to prevent the shutter from being unintentionally removed from rectangular opening 54.

The Prism System

Sample 10 can be viewed through the opening in the upper surface 40 of base 19 when shutter 56 is open. However, if an operator were required to view sample 10 along a straight line, the operator's viewing position would be undesirably lower than the normal viewing position of the operator, which is established by the location of sample support 35. A prism 57 is mounted on the upper surface 40 of base 19 to raise the viewing position of the operator to a convenient height. Prism 57 may be a conventional 90°, 45°, 45° prism and the portion of base 19 under prism 57 may be formed by a wedge shaped portion 58 (shown in FIG. 2 but not shown in FIG. 1) that further adjusts the viewing position, which is shown at point 58 in the drawing. Dashed lines 60 from sample 10 to viewing position 62 illustrate the effect of the prism in raising the viewing position. Dashed lines 64 also show the apparent line of sight of a viewer, and a view of the test subject in the position seen by the viewer is shown as image 66 in FIG. 2. Thus, this position is very nearly the position that an operator would use if the probe head were removed and the test subject were viewed directly. As the textile 10 is moved to various locations at which a test might be made, the operator is given a closely natural view of the test subject that facilitates the manual operations that are required for moving the test subject 10 to various locations that might be selected for the test.

As FIG. 1 shows, the front edge 70 of the prism and the front edge of the opening 52 in base 19 are located as close as possible to cavity 25 and are located as close as possible to cavity 25 to give the operator a view of the test subject that is as nearly a top view as is possible. The length of opening 52 between the front edge 70 and the back edge 72 is selected to give the operator a satisfactorily full view of the test subject; as FIG. 1 shows, the width of the opening is slightly less than the diameter of cavity 25. The height of the shutter opening 54 as seen in FIG. 2 is selected to provide a maximum viewing aperture but to maintain a sufficient thickness of the base for supporting probe head support 12 and slide 30. The horizontal width of shutter opening 54 as seen in FIG. 2 is established by the length of the cord that is formed by the intersection of rectangular opening 54 and cylindrical cavity 25.

Prism 57 can be mounted on base 19 by any suitable means. For example (not shown in the drawing), a notched bar can be positioned along the upper edge 68 of the prism and the bar can be connected to base 19 by means of a screw located on either side of the prism.

In the preferred probe head assembly, the shutter is located in a position to possibly interfere with the cutout 80 portions that are formed in base 19 to provide optical clearance for light to fiber optic bundles 14 thru 17. Corresponding cutout portions 82 are formed in the shutter, as can be seen in FIG. 1. (Notice that the orientation of the peripheral fiber optic bundles 14–17 has been rotated by 45° in FIG. 2 to simplify the drawing.)

As an additional feature of the apparatus of the drawing, several slides 30 can be provided with differing sizes for the aperture of reference plate 32 for performing the color test on a small selected area of a subject. Typical sizes are between ¼ inch and 1 inch in diameter. The base 19 is constructed to permit convenient operation of both the slide 30 and the shutter mechanism.

From this description of a preferred embodiment of the invention, those skilled in the art will recognize a variety of modifications within the spirit of the invention and the scope of the claims.

What is claimed is:

1. In a color analyzer of the type having a probe head, a base forming a cavity for the probe head, means for positioning a subject such as a textile to be analyzed adjacent to the base at the end of the cavity opposite the probe head for a color analyzing operation on the subject, means for supporting the base for a sample to be at approximately hand level and slightly below eye level for a seated operator, improved apparatus for use by the operator for viewing the sample at the position at which the color analysis is to be made, comprising, a shutter mechanism and means in said base for guiding said shutter mechanism along a path between an open position and a closed position, the path intersecting a portion of the cavity, said shutter having a surface conforming to the shape of the cavity when the shutter is in the closed position, means in said base forming an optical pathway between said cavity and an upper surface of the base when the shutter is in its open position, and a prism mounted on said base over said pathway to provide an image of the textile to be analyzed at a convenient viewing height when the shutter is open.

2. The apparatus of claim 1 wherein said cavity is a cylindrical cavity and said surface of said shutter is an arcuate surface conforming to said cylindrical cavity when the shutter is in the closed position.

3. The apparatus of claim 2 wherein
said shutter mechanism comprises a bar shaped, non-reflective, element with said arcuate surface, said bar having an inner end and an outer end and having a handle mounted on said outer end,
said base having an opening that is generally rectangular in cross section extending from its righthand side (as viewed from the operator's position) forming said means for guiding the shutter mechanism.

4. The apparatus of claim 3 wherein the probe head of the color analyzer has a generally disk shaped support with a plurality of fiber optic bundles located at about the periphery of the cavity at an angle of about 45° to the axis of the cavity, including at least one fiber optic bundle located in the sector intersected by said shutter mechanism, and said base has cut out portions at the rim of the cavity at the location of the peripheral fiber optic bundles, wherein
said shutter mechanism has cut out portions at the rim of said arcuate surface to correspond with the cut out portions of the base in the sector of the shutter mechanism.

5. The color analyzer of claim 3 wherein
said prism is a 90°, 45°, 45° prism, and
said upper surface of the base is a substantially flat surface with a portion in the region of the prism angled slightly downward from the horizontal toward the operator to adjust the viewing position to the convenient height.

6. The apparatus of claim 3 wherein said color analyzer includes a slide and means for positioning said slide at said opposite end of said cavity and wherein said means in said base forming said passageway between the cavity and the upper surface of the base includes a portion forming a lower surface of said optical pathway and extending over said slide for supporting said slide.

7. The apparatus of claim 6 wherein said means for positioning said slide includes means forming a guideway in said base at said opposite end of said cavity and extending partly under said opening in said base for said shutter mechanism, said slide being adapted to be removed from said base on the side opposite said handle of said shutter mechanism.

* * * * *